United States Patent [19]

Queen

[11] 4,399,101
[45] Aug. 16, 1983

[54] STOPPED-FLOW APPARATUS

[76] Inventor: Alan Queen, 35 Purdue Bay, Winnipeg, Manitoba, Canada, R3T 3C6

[21] Appl. No.: 271,820

[22] Filed: Jun. 9, 1981

[30] Foreign Application Priority Data

Jun. 10, 1980 [GB] United Kingdom ................ 8018897

[51] Int. Cl.³ ............................................. G01N 21/75
[52] U.S. Cl. ...................................... 422/68; 356/410; 356/440; 422/50; 436/34
[58] Field of Search ...................... 422/50, 64, 68, 224, 422/100; 356/246, 410, 440; 250/461 C; 436/34

[56] References Cited

U.S. PATENT DOCUMENTS

| | | | |
|---|---|---|---|
| 3,711,206 | 1/1973 | Moran | 356/246 X |
| 3,854,878 | 12/1974 | Kiesow | 422/68 |
| 3,932,136 | 1/1976 | Stickney | 422/224 |
| 3,970,388 | 7/1976 | Hacker | 356/246 |
| 4,086,061 | 4/1978 | Hoffa et al. | 422/68 |

OTHER PUBLICATIONS

Biochem., 1964, (91), pp. 161-171, Gibbons et al.

Primary Examiner—Michael S. Marcus
Attorney, Agent, or Firm—Stanley G. Ade

[57] ABSTRACT

A stopped-flow apparatus is disclosed which includes one or a pair of flow systems mounted in separate thermostatically controlled baths and actuated by a single driving system thus permitting differential rate of determinations. The reaction or observation cell is easily changed to modify the apparatus without the necessity of changing the entire flow system. This is accomplished by screw threaded connection to the cell so that a variety of different cells can be inserted readily and easily into the thermostatically controlled bath. Stopping is accomplished by means of an adjustable block system on the main driving system or by a stopping syringe operatively connected to the cell. Efficient mixing is accomplished in a mixing chamber screw threadably secured to the cell and utilizing a double bifurcated feed block.

6 Claims, 11 Drawing Figures

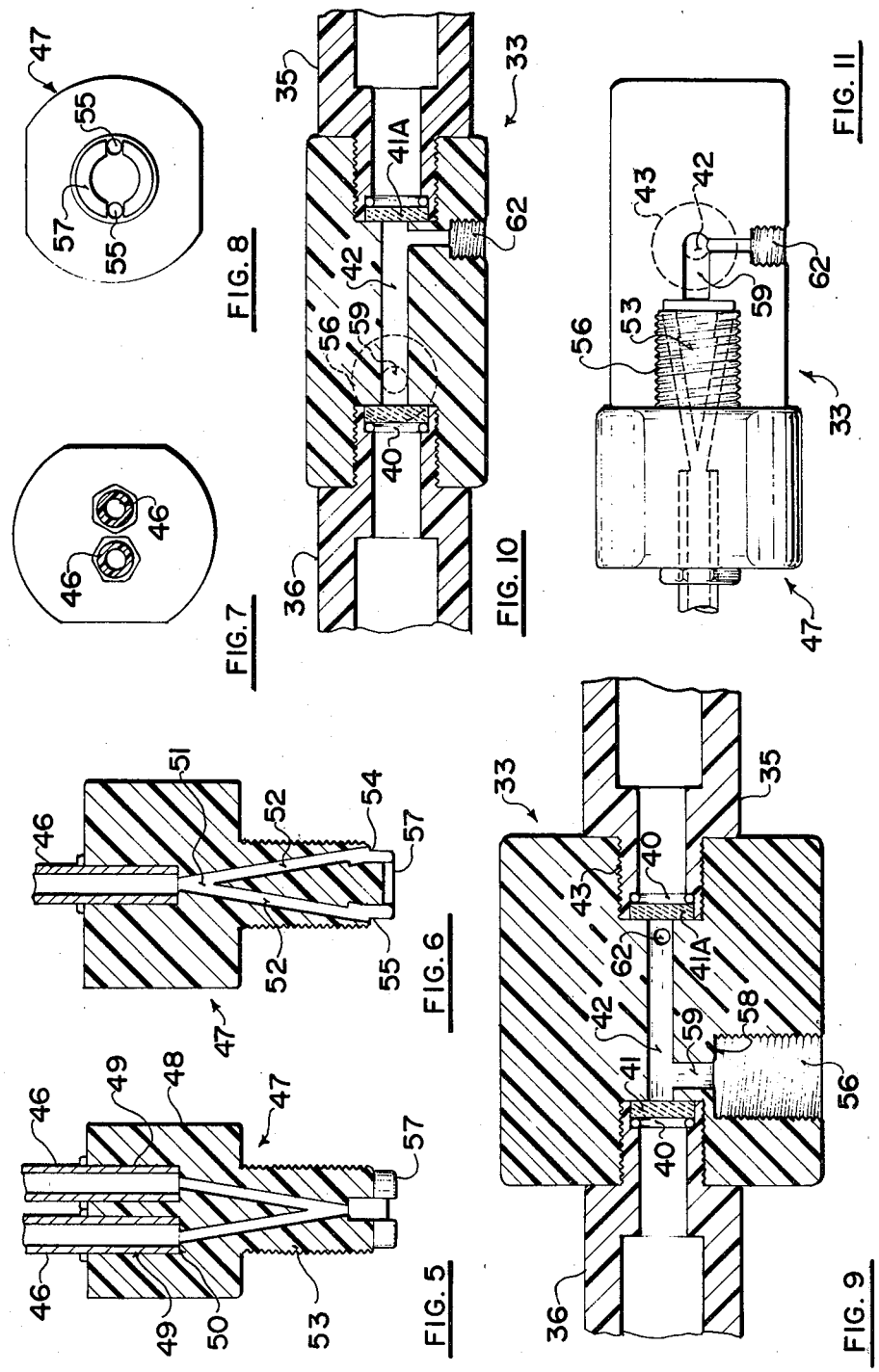

STOPPED-FLOW APPARATUS

BACKGROUND OF THE INVENTION

Fast chemical reactions may be initiated by rapidly mixing two reactants. The reactions may, in principle, be followed in one of two main ways. The first of these, called the continuous-flow method, employs standard detection techniques (as distinct from fast ones) but has the serious drawback of consuming relatively large amounts of reagents. Advances in electronics and the techniques for rapidly collecting data have caused the continuous-flow method to become less important than the stopped-flow technique, which uses relatively small amounts of the reagents.

In the stopped-flow apparatus, the reagents are stored in a pair of syringes which, to initiate the reaction, are driven forward by means of a hydraulic or pneumatic piston. The reactants then mix in a small mixing chamber before entering the reaction or observation cell where the course of the reaction is followed by an appropriate method. As the freshly mixed solution enters the reaction cell, the solution already there is forced into a third syringe (called the stopping syringe). The plunger of this syringe is thus driven onto a fixed stopping block which brings the flow of reagents to an abrupt stop. At this instant, a micro-switch is closed to trigger an electric impulse to start data collection.

All stopped-flow machines have these features in common. The various models usually differ only in the design and construction of the mixer, reaction cells and methods of detecting chemical changes.

The first commercially available stopped-flow apparatus, which is still the most popular one, was produced by the Durrum Instrument Company. It is based on a published design by Gibson and Milnes (Biochem. J. Vol. 91, 161 (1964)). Moderately satisfactory temperature control is achieved by circulating water through the metal block enclosing the reaction cell and by immersing the driving syringes in a shallow bath through which the same water is circulated. The apparatus has an excellent four or eight jet mixer close to the reaction cell, which has a long light path to enable studies with dilute solutions to be carried out. The flow system is mounted on a rigid metal casting to minimize effects due to vibrations set up when the flow is stopped. The standard apparatus has a set of adjustable mirrors which enable it to be used for both transmission and fluorescence studies. It is also available with a cell containing electrodes for temperature-jump work.

The main disadvantages of the apparatus are:
1. Temperature control is not good enough for many studies in physical and analytical chemistry. This deficiency could only be rectified by redesigning the apparatus.
2. The reaction cells cannot be readily changed or modified to permit other means of detecting chemical changes.
3. Corrosion of the valve stems and the plungers of the syringes is a frequent problem unless care is taken to dismantle and clean the apparatus regularly.

The American Instrument Company has introduced a stopped-flow apparatus with a number of attractive features such as small volume and easy attachment to different types of commercial spectrophotometers. Unfortunately, the apparatus has a number of undesirable weaknesses:

1. Temperature control is hopelessly inadequate for precision work, despite the fact that thermostatted liquids may be circulated through the metal block in which the flow system is mounted. Part of the problem is that the plastic flow system and syringes are poor thermal conductors and the apparatus has no provision for preequilibrating the solutions.
2. In use, the O-rings set in the Kel-F (trade mark) syringes soon become compressed and the apparatus develops leaks. This is not permissible in a stopped-flow apparatus. The problem becomes very pronounced when work is carried out at different temperatures, due to the different coefficients of expansion of the syringes and the O-rings.
3. Provision is made in the apparatus for detecting light changes at right angles to the beam of light from the monochromator. However, many users of the apparatus have found that studies of light scattering or fluorescence are not possible owing to the fact that the Teflon (trade mark) parts of the reaction cell fluoresce very strongly.

In 1974, Caldin, Crooks and Queen described a stopped-flow apparatus which, apart from the Teflon (trade mark) keys of the three-way stopcocks, was made entirely of glass or quartz. The syringes and stopcocks were mounted on a platform and connected by narrow bore glass tubes to the mixer and reaction cell which were suspended on mounts below the platform. The reaction chamber was connected to a source of monochromatic light and a photomultiplier by means of fibre-optic light guides (J. Phys. E., Scientific Instruments. 6, 930 (1973)). This arrangement allowed the mixer and reaction chamber to be immersed in a well-controlled constant temperature bath.

This apparatus is now commercially available from Nortech Laboratories U.K. In terms of temperature control and ease of use it is probably the most reliable apparatus available. The apparatus is constructed in modules. The driving piston and its controls, as well as the stopping block and triggering microswitch, are common to all machines. A number of different flow modules are available for light transmittance, fluorescence and temperature-jump studies. The apparatus is, therefore, quite versatile. However, each of the various modules is suitable for only one type of study and each one is quite expensive. The versatility of this apparatus is only available at considerable cost.

SUMMARY OF THE INVENTION

The stopped-flow apparatus of this present application overcomes many disadvantages of previous apparatus and includes the following details and advantages:
1. The whole flow system is made of glass, quartz, Teflon (trade mark) or Kel-F (trade mark). This ensures chemical inertness towards most materials.
2. The storage reservoirs and the flow system are enclosed in a thermostatted bath whose temperature can be accurately adjusted, controlled and quickly changed as required. Temperature control to $+0.005°$ C. has been achieved in the range $-10°$ to $+60°$ C.
3. The driving and stopping syringes, which are made of glass with Teflon (trade mark) luer-loc tips, are commercially available in different sizes. They may be easily interchanged to permit different volumes of the reagents to be mixed.
4. The mixer is a specially designed unit to which reaction cells of different designs and materials can be quickly and firmly attached. In the mixer, double mixing of the reagents is achieved in about 1-2 milliseconds by dividing each stream of reagents before mixing them, at the entrance to a small mixing chamber, where the second mixing occurs. This chamber is situated at the entrance to the reaction cell. The overall dead-time when this mixer is attached to a reaction cell of 2 mm bore and 10 mm length is about 4 milliseconds when the driving cylinder is actuated by an air pressure of 20 lbs./sq. in.

5. The pneumatic driving piston is of large bore and turbulent flow of the reactants is achieved at pressures between 15-20 lbs./sq.in. Such low pressures minimize problems due to shock waves, generated in most stopped-flow machines when the flow is abruptly halted. Shock waves are also further decreased in the present machine by the use of Teflon (trade mark) tubing between the syringes and the reaction chamber.

6. A particularly important feature of the apparatus is that a number of different kinds of reaction cells are available. These can be easily and rapidly interchanged. This feature differs from conventional apparatus in that only the reaction cell and not the complete flow system is changed on order to modify the apparatus. At the present time, the following cells are available:

A. A Teflon (trade mark) cell of 2 mm bore and 10 mm length, fitted with quartz window.

B. Similar cells of 2 and 5 mm length.

C. A quartz cell with light paths of 2 and 10 mm length which can be used for measuring changes in light transmission, light scattering and fluorescence.

D. A conductance cell with platinum electrodes. A conductance bridge is available for use with this cell.

The following accessories may be incorporated:

E. A cell for measuring changes in optical rotation.

F. A temperature-jump cell.

A recent review (Applied Spectroscopy Reviews. 13, 165 (1977)) has emphasized the need in analytical chemistry for a stopped-flow apparatus which can be fitted with automatic valves to control the supply of different reagents and to switch the machine from the "load" condition to the "operate" condition under the control of a microcomputer. The authors of this review stress that the present manufacturers of stopped-flow machines do not provide such capabilities for their equipment. Furthermore, the presently available machines cannot be easily modified for automatic operation. The present apparatus is designed with this possibility in mind and it is quite easy to replace the standard valves with automatic models (e.g. Rheodyne model 5003) or simply to attach automatic actuators to the standard apparatus. Such actuators are commercially available and a special device is designed to fit the apparatus.

The apparatus may also be constructed with two flow systems, mounted in separate thermostat baths and actuated by a single driving piston. This arrangement permits differential rate determinations. The differential technique results in an increase in accuracy for experiments where data are obtained from the calculation of differences in rate constants. Thus, the method and apparatus is particularly useful for determining small isotope effects and the effects of temperature on chemical reactions.

In accordance with the invention there is provided a stopped-flow apparatus for observing and measuring the rates of fast reactions in solutions, comprising in combination supporting structure, at least one flow system on said supporting structure, said flow system including a temperature controlled enclosure on said supporting structure, a reaction cell detachably supported within said enclosure, a mixing chamber detachably connected to said reaction cell, at least two syringe assemblies operatively connected to said mixing chamber, means to supply said syringes with solutions to be mixed in said mixing chamber, a drive system for said syringes, adjustable stopping means operatively connected to said flow system, a light source operatively connected to said reaction cell, reaction detection means also detachably secured to said reaction cell, and drain means detachably secured to said reaction cell, said mixing chamber, said light source, said detachable means and said drain means all being screw threadably secured to said cell in operative relationship thereto for facilitating connection and disconnection therewith.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

FIG. 5 is a partially schematic cross sectional side elevation of the mixing chamber per se.

FIG. 6 is a view at right angles of FIG. 5.

FIG. 7 is a top plan view of FIG. 5.

FIG. 8 is an underside view of FIG. 6.

FIG. 9 is a cross sectional top plan view of the observation or reaction cell per se.

FIG. 10 is a side view of FIG. 9.

FIG. 11 is an end view of FIG. 9.

In the drawings like characters of reference indicate corresponding parts in the different figures.

DETAILED DESCRIPTION

Figure 1:
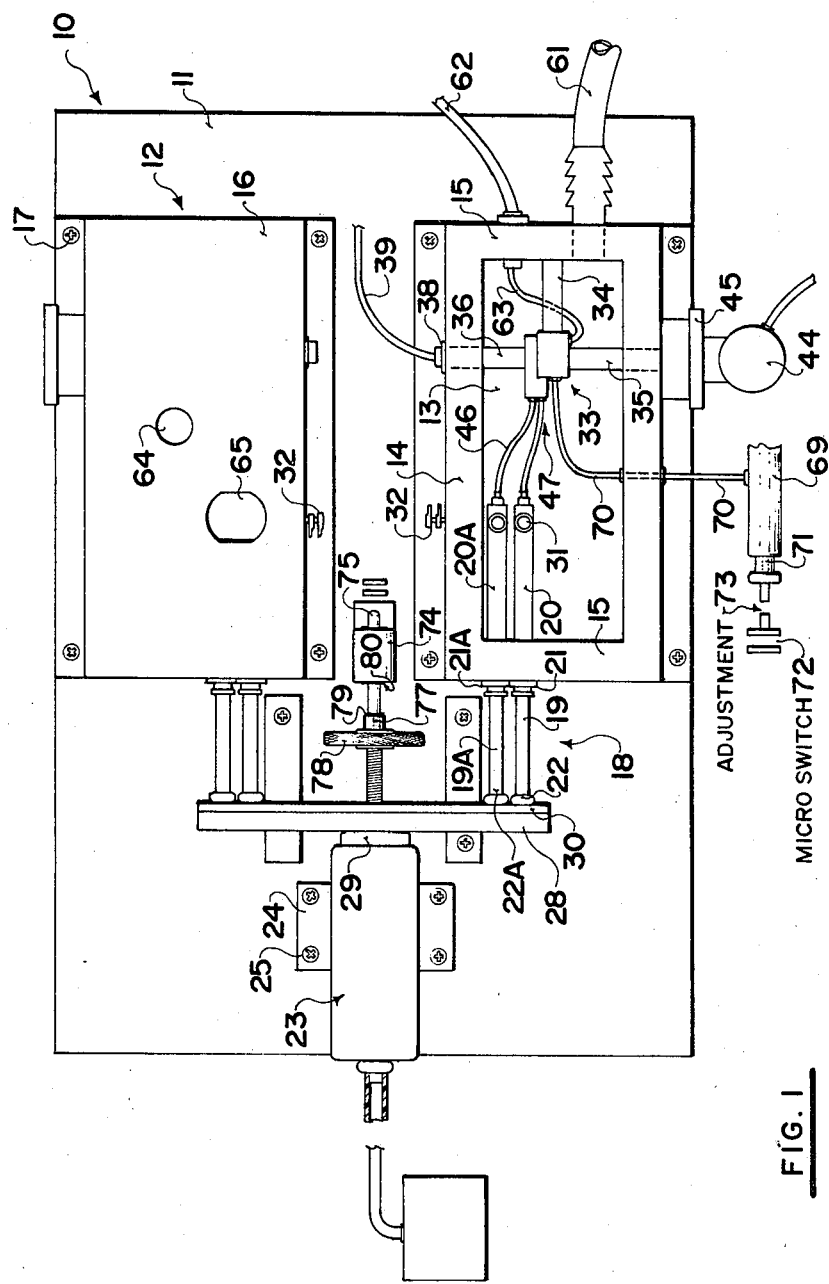
FIG. 1 is a partially schematic top plan view of the apparatus showing one of the reaction vessels with the cover in place and the other with the cover removed for clarity.
Figure 2:
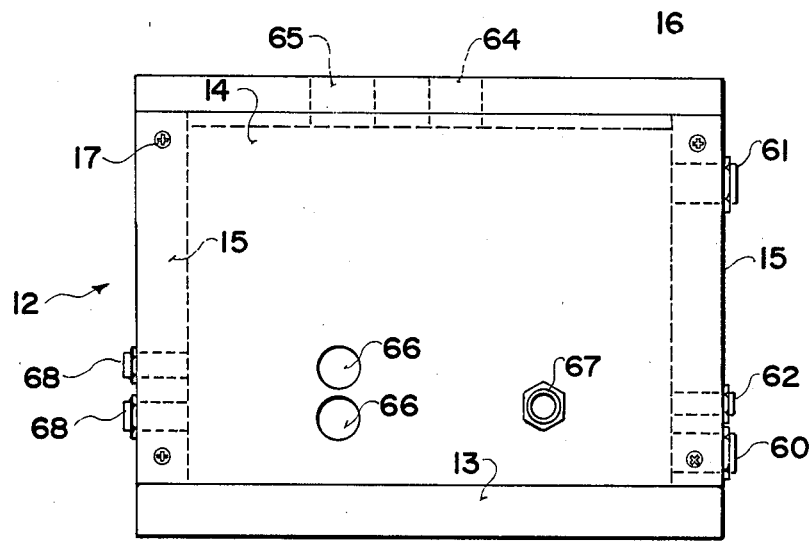
FIG. 2 is a side view of one of the reacting vessels per se.
Figures 3, 4:
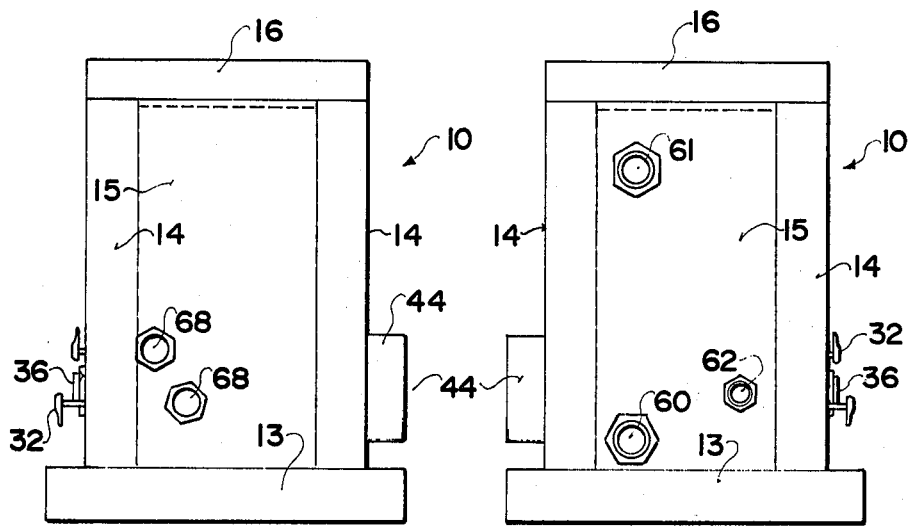
FIG. 3 is a view of one end of FIG. 2.
FIG. 4 is a view of the other end of FIG. 2.

Proceeding therefore to describe the invention in detail, reference should first be made to FIG. 1 in which supporting structure collectively designated 10 includes a base 11 upon which a pair of reaction vessels are mounted collectively designated 12. These are identical in construction and each includes a base 13, side walls 14, end walls 15, and a detachable cover or upper wall 16, detachably secured to the upper sides of the side and end walls by means of screws 17 or the like.

Although the apparatus can be made with a single reaction vessel, nevertheless it is desirable that a pair of such vessels be provided in side by side relationship as illustrated.

Under these circumstances, a flow system is provided for each, collectively designated 18 with each flow system consisting of a pair of syringes 19 and 19A situated in side by side relationship adjacent one end wall 15 of the reaction vessel. Each syringe includes a barrel 20, 20A within the interior of the reaction vessel and being secured through the end wall 15, by means of clamp members 21 or the equivalent with the plungers or piston rods 22 extending therefrom in spaced and parallel relationship as clearly shown.

Means are provided for driving the four plungers simultaneously, said means taking the form of a drive piston and cylinder assembly collectively designated 23 and mounted upon the base 10 by means of plate 24 and screws 25. This drive assembly includes a cylinder 26 with a piston rod or triggering rod 27 extending therefrom. It is operatively connected to a source of fluid under pressure such as a compressed air tank 26 situated remotely from the apparatus and connected thereto by means of flexible tubing 27. A suitable control valve (not illustrated) is operatively connected between the compressed air tank 26 and the drive means 23 in order to operate same as required. Such valve is conventional and it is not believed necessary to show same.

A cross head type driving block 28 is secured to the distal end of the piston 29 of the assembly 23 with the triggering arm or rod 27 extending from the front end of this driving block. The driving block includes a vertical flange 30 engaging the distal end of the plungers 22 of the four syringes 18 so that when the drive piston and cylinder 23 is actuated, all four plungers are driven simultaneously.

Each syringe barrel 20 is provided with a reservoir shown schematically by reference character 31 which holds the reaction solutions and these are controlled by three-way valves 32 so that the syringes can be filled with the required amounts of the various reaction solutions whereupon they can be shut off by the valves 32 to seal the barrels. Such apparatus is conventional and well known, and it is not believed necessary to describe same further.

Detachably supported within the reaction vessel is the observation chamber or reaction cell collectively designated 33 and shown in detail in FIGS. 9, 10 and 11. It is detachably supported within the enclosure 12 by means of a solid rod 34 which screw threadably engages within one side of the cell body and which engages in one end wall 15 of the enclosure to which it may be held by a clamp gland nut (not illustrated).

A further pair of supports take the form of hollow support arms or rods 35 and 36 extending diametrically opposite one another from the cell into which they are screw threadably engaged as will hereinafter be described with reference to FIGS. 9, 10 and 11. These hollow rods engage through apertures within the side walls 14 of the reaction vessel enclosure and are detachably clamped in position by means of clamp gland nuts (not illustrated).

The cell is formed preferably from a block of glass impregnated Teflon (trade mark) forming an observation chamber. Screw threaded apertures 37 are formed in diametrically opposite sides of the block and screw threadably receive the screw threaded inner ends of the hollow support arms 35 and 36. A further aperture (not illustrated) and also screw threaded, is formed in the end wall of the block to screw threadably receive the solid support rod 34.

A light pipe barrel 38 connects a light pipe 39 through one side wall of the enclosure and into the inner end of the hollow support arm 36, being sealed by means of an O-ring 40 at the inner end thereof with the base of the screw threaded aperture 37 being provided with a quartz window 41 communicating with a light path channel or bore 42 which extends through the block to a further quartz window 41A at the base of the screw threaded aperture 42 into which the hollow support 35 is engaged. This permits operative connections to a photomultiplier 44 (see FIG. 1) and, if desired, camera shutter arrangement 45.

Once again an O-ring 40 is provided adjacent the base of the screw threaded aperture 42.

Teflon (trade mark) tubing 46 connects the discharge end of the syringe barrels 20 and 20A, to a mixing chamber collectively designated 47 and shown in detail in FIGS. 5–8.

This mixing chamber is preferably formed from Teflon (trade mark) in the form of a block 48 having a pair of inlet bores 49 into which are detachably clamped, the ends of the tubing 46 extending from the two barrels 20 and 20A. A conventional form of clamps (not illustrated) may be provided to detachably retain the ends of these tubes within the inlet bores 49.

At the inner end 50 of each bore 49, there is provided a bifurcated bore or drilling system shown in FIG. 6 with one end 51 being connected to each inner end 50. The two legs 52 of these bifurcated bores extend through the screw threaded shoulder portion 53 of the mixing chamber to adjacent the distal end 54 thereof, one upon each side of this shouldered portion 53 and the corresponding legs of the bifurcated bore, extending from each of the bores 49 converge and meet at this inner end at a common locus identified by reference character 55. These meeting points 55, from each of the tubes 46, constitute a first mixing point, one upon each side of the shouldered portion 53. This screw threaded shouldered portion screw threadably and detachably secures the mixing chamber into the cell at the screw threaded aperture position 56 shown in FIGS. 9, 10 and 11 and it will be noted that a relatively short outer end cylindrical portion 57 is provided as an extension to the screw threaded shoulder 23 and that this abuts against the inner end 58 of the screw threaded bore or aperture 56. A relatively short bore or drilling 59 extends from the base 58 to the light path bore 42 and this constitutes a second point of mixing thus ensuring a full mixing of the two solutions takes place immediately prior to them entering the light path bore 42 at which point they are stopped as will hereinafter be described.

It will be appreciated that the cell 33 is easily removed and replaced merely by loosening the gland nuts of the support rods 34, 35 and 36 whereupon the cell may be lifted clear, still connected by the flexible tubing 46 to the syringes. The support rods may then be unscrewed and the mixing chamber may also be unscrewed thus enabling the cell to be removed and replaced readily and easily.

The temperature of the cell is controlled by cooling water entering the enclosure or reaction vessel via a connection 60 through one end wall of the vessel and circulating through the vessel to exit through another connection 61 also within the end wall 11 of the vessel.

Spent solution from the cell 33 may be conveyed through the wall via a connection 62 and be connected to the cell by means of a short length of flexible tubing 63 readily attached and detached from the cell by conventional means.

A thermometer may be mounted upon the reaction vessel through an aperture 64 in the cover or lid 16 thereof and the reservoir may be accessed through an aperture 65 which may be detachably closed by means (not illustrated).

Apertures in the side of the vessel indicated by reference character 66, permit access to the three-way valve with apertures 67 receiving the hollow support arm 36. Apertures 68 receive the syringe barrels 20 and 20A.

Two means are provided for stopping the flow of the solutions from the syringes 20 and 20A when the drive means 23 is actuated.

Firstly, a conventional stopping syringe 69 may be provided connected via flexible tubing 70, to the cell 33. As the solutions are driven from the syringe barrels 20 and 20A, into the mixing chamber and thence into the cell 33, solution already in the cell is driven through tubing 70, to the syringe 69 thus extending the plunger 71 and actuating a microswitch 72 which is operatively connected to the reaction detection means such as photomultiplier 44. An adjustment 73 is provided to adjust the distance moved by the plunger 71 before it actuates switch 72.

The second and preferred embodiment is particularly useful when a pair of flow systems is actuated simultaneously for differential rate determinations and the like. As mentioned previously, the differential technique results in an increase in accuracy for experiments where data are obtained from the calculation of differences in rate constants.

In this embodiment, the cross head stopping block 28 actuates the four plungers as hereinbefore described and the stopping rod 27 slidably engages through an apertured stopping block 74 mounted upon the base 11 with the inner end of the rod 27 being screw threaded as indicated. The distal end 75 of the rod 27 operatively engages a microswitch 76 operating in a manner similar to microswitch 72 hereinbefore described and controlling the reaction detection means.

Once again, the effective distance moved by the piston of the drive means 23, is controllable by a collar 77 secured to a knurled wheel 78 with the collar being screw threadably engageable upon the screw threaded inner end portion of the rod 27. The outer side or end 79 of the collar strikes the end 80 of the block thus stopping the action immediately so that the distance travelled by the solutions through the mixing chamber and into the cell, may be controlled accurately.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. Stopped-flow apparatus for observing and measuring the rates of fast reactions in solutions comprising, in combination, supporting structure, at least one flow assembly on said supporting structure, said flow assembly including a temperature controlled enclosure on said supporting structure, a reaction cell detachably supported within said enclosure, a mixing chamber detachably and operatively connected to said reaction cell, at least two syringe assemblies mounted on said supporting structure and being operatively connected to said mixing chamber, means mounted on said supporting structure to supply said syringes with solutions to be mixed in said mixing chamber, a drive system for said syringes being operatively connected thereto, adjustable stopping means on said support structure operatively connected to said reaction cell, and drain means detachably secured to said reaction cell; said mixing chamber, said light source, said detachable means and said drain means all being screw threadably secured to said cell in operative relationship thereto for facilitating connection and disconnection therewith, said mixing chamber including a block, inlet means on one side of said block and outlet means on the other side thereof screw threadably connectable to said cell, said inlet means including means operatively connecting same to each of said syringes, a bifurcated bore in the shape of an inverted V extending from each of said means operatively connecting said inlet means to each of said syringes, each leg of said bifurcated bore communicating at the end thereof with a different side of the inner end of said outlet means and with the end of the leg of the other bifurcated bore to form a first point mixing, one mixing zone upon each side of said inner end of said outlet means, and being substantially diametrically located within said block forming said mixing chamber, the outer end of said outlet means constituting a second point mixing at the area of connection of said outlet means to said cell.

2. The apparatus according to claim 1 which includes a pair of separate flow systems in said supporting structure in side by side relationship, and separate temperature control means for each of said systems, said drive system being operatively connected to both of said flow systems for concurrent operation thereof.

3. The apparatus according to claim 2 in which said drive system includes a drive piston and cylinder assembly, pressure fluid means operatively connected thereto for operating same, a cross head drive block operatively connected to the piston of said drive system, said drive block being operatively connected to the plungers of said syringes of each of said flow systems.

4. The apparatus according to claim 1, 2 or 3 in which said adjustable stopping means includes a stopping syringe in said supporting structure operatively connected to said cell, switch means operatively connected to the plunger of said stopping syringe, and to said reaction detection means and adjustable means between said plunger and said switch means.

5. The apparatus according to claim 3 in which said adjustable stopping means includes a triggering rod extending from said piston of said drive piston and cylinder assembly, an apertured stopping block in said supporting structure, the distal end of said triggering rod slidably engaging therethrough, switch means adjacent the distal end of said triggering rod and actuated by the distal end thereof and being operatively connected to said reaction detection means, and adjustable means along said triggering rod engageable with said stopping block to control the distance travelled by said piston rod, said adjustable means including a collar screw threadably engaging a screw threaded portion of said piston rod, said collar engaging said stopping rod when said piston rod is extended.

6. The apparatus according to claim 1, or 3 in which said means for detachably supporting said reaction cell within said enclosure includes a first support arm detachably secured to said cell and extending therefrom, means detachably clamping the distal end of said first support arm in the wall of said enclosure, a second hollow support arm detachably secured to said cell, means detachably clamping said second hollow support arm through the wall of said enclosure, and a third hollow support arm detachably secured to said cell diametrically opposite to said second hollow support arm, said third hollow support arm also extending through the wall of said enclosure and being detachably clamped thereto, said reaction detection means being operatively connected to said cell through one of said hollow support arms, and a light source operatively connected to said cell through the other of said support arms, a light path bore extending through said cell and operatively connecting said light source with said reaction detection means and means operatively connecting said mixing chamber with said light path bore.

* * * * *